(12) United States Patent
Liprie

(10) Patent No.: US 6,485,405 B1
(45) Date of Patent: **\*Nov. 26, 2002**

(54) METHOD OF MAKING A SOURCEWIRE WITH INTEGRAL CAPSULE

(75) Inventor: Sam F. Liprie, Lake Charles, LA (US)

(73) Assignee: Interventional Therapies, LLC, Westport, CT (US)

( * ) Notice: Subject to any disclaimer, the term of this patent is extended or adjusted under 35 U.S.C. 154(b) by 17 days.

This patent is subject to a terminal disclaimer.

(21) Appl. No.: 09/627,755

(22) Filed: Jul. 28, 2000

Related U.S. Application Data

(60) Provisional application No. 60/146,259, filed on Jul. 29, 1999.

(51) Int. Cl.[7] .................................................. A61N 5/00
(52) U.S. Cl. .......................................................... 600/3
(58) Field of Search ........................................ 600/1–8

(56) References Cited

U.S. PATENT DOCUMENTS

| | | |
|---|---|---|
| 3,351,049 A | 11/1967 | Lawrence |
| 4,763,642 A | 8/1988 | Horowitz |
| 4,861,520 A | 8/1989 | Van't Hooft et al. |
| 4,891,165 A | 1/1990 | Suthanthiran |
| 5,084,002 A | 1/1992 | Liprie |
| 5,141,487 A | 8/1992 | Liprie |
| 5,163,896 A | 11/1992 | Suthantiran et al. |
| 5,282,781 A | 2/1994 | Liprie |
| 5,342,283 A | 8/1994 | Good |
| 5,395,300 A | 3/1995 | Liprie |
| 5,454,794 A | 10/1995 | Narciso et al. |
| 5,520,194 A | 5/1996 | Miyata et al. |
| 5,833,593 A | 11/1998 | Liprie |
| 6,283,910 B1 | 9/2001 | Bradshaw et al. |

Primary Examiner—John P. Lacyk
(74) Attorney, Agent, or Firm—Cantor Colburn LLP

(57) ABSTRACT

There is disclosed a method of forming a radioactive sourcewire and a radioactive sourcewire formed according to the preferred method. The method generally includes providing a substantially thick walled tubular member and drilling or counterboring an enlarged cavity in a distal end of the tubular member. A radioactive source is inserted into the tubular member and the distal end of the cavity is sealed shut. During drilling of the cavity, material removed from the inside of the cavity may be allowed to flow to the space between the bore of the tubular member and the cavity thereby to form a plug. Finally, the proximal end of the tubular member may be sealed shut.

56 Claims, 1 Drawing Sheet

METHOD OF MAKING A SOURCEWIRE WITH INTEGRAL CAPSULE

RELATED APPLICATIONS

The present application claims priority to U.S. Provisional Application 60/146,259, filed Jul. 29, 1999 and entitled "Method of Making a Sourcewire with Integral Capsule," the entire contents and disclosure of which are herein specifically incorporated by reference.

TECHNICAL FIELD

The technical field relates generally to radioactive sourcewires for treatment of diseases, and, more particularly, to a flexible sourcewire for use in radiation therapy after an angioplasty procedure in order to minimize the occurrence of restenosis.

BACKGROUND OF THE INVENTION

During or after the performance of a percutaneous transluminal angioplasty procedure to relieve a constriction within a patient's vessel, it has been found beneficial to irradiate the site of the constriction to prevent reclosure or restenosis due to smooth muscle cell proliferation. Typically, a catheter having a blind lumen extending to a distal end thereof is advanced to the treatment site and a sourcewire having a radioactive tip is advanced to the treatment zone of the catheter adjacent the treatment site within the vessel. This is typically accomplished by connecting a proximal end of a catheter to a mechanism for advancing the sourcewire, such as an afterloader, and operating the afterloader to advance the sourcewire to the treatment site.

Commonly, in afterloaders, the sourcewire is substantially wound about a reel or spool with only the distal end, that end containing the radioactive source, left in a straight or uncoiled position. The radioactive source is typically housed within a shielded container provided on the afterloader. In operating the afterloader, the sourcewire is unraveled off the reel and advanced through the catheter down the various narrow or tortuous pathways to reach the arteries and, in particular, the remote coronary arteries. Sourcewires may be repeatedly used over again until such time as the radioactive level of the radioactive source is of no further beneficial use.

During the repeated cycling of the sourcewire about the reel and through the catheter to reach the coronary arteries, the sourcewire is subjected to various stresses and strains along its length thereof. This may pose problems in particular sourcewire constructions which can result in cracking, buckling or kinking at various positions along the sourcewire. In one known sourcewire construction, the sourcewires are formed by having a thin walled tube with a substantially full length backbone wire affixed therein. The backbone wire terminates short of the distal end of the tube to define a cavity for receipt of a radioactive source or sources therein. The backbone wire construction of the radioactive sourcewire provides the advantage of allowing a relatively long treatment zone to be provided by the tube defining the cavity at a distal end thereof. Alternatively, sourcewires formed from an entirely solid wire having a drilled distal end for receipt of a radioactive core are known. The solid wire construction is less prone to damage from repeated cycling. However, when constructing sourcewires of relatively small diameters, i.e. generally less than 0.014 of an inch, it becomes difficult to drill a cavity into the solid wire of sufficient length to accommodate the desired longer radioactive sources.

Thus, there exists a need for a radioactive sourcewire combining the strength and flexibility of a substantially solid wire along the predominant length thereof as well as having a tubular construction at a distal most end to accommodate varying lengths of radioactive sources.

SUMMARY OF THE INVENTION

The above discussed and other drawbacks and deficiencies of the prior art are overcome or alleviated by the radioactive sourcewire and method for forming a radioactive sourcewire of the present invention. The present method for forming a radioactive sourcewire includes providing a generally elongated thick walled tubular member and drilling an enlarged cavity in the distal end of the tubular member. The cavity is of sufficient length to retain a radioactive source. During drilling of the cavity, material removed from the tubular member to form the cavity is preferably allowed to flow from the cavity and into a bore of the elongated tubular member to thereby form a plug and to seal the cavity from the bore. A radioactive source may then be inserted into the cavity either in a radioactive state, in which case the source is preferably coated with a neutron permeable material, or an inert state. The distal end of the tubular member is then welded or otherwise sealed shut to seal the radioactive source within the cavity. Finally, the proximal end of the elongated tubular member may also be welded or otherwise sealed shut.

The disclosed sourcewire generally includes an elongated tubular member having a substantially elongated bore of a first diameter and an enlarged cavity formed in the distal end of the tubular member having a diameter greater than that of the first diameter. A radioactive source is positioned within the cavity and the distal end of the elongated tubular member is sealed, preferably by being welded shut, or by other methods. Preferably, the sourcewire additionally includes a plug between the bore of the elongated tubular member and the enlarged cavity. Further, the plug may preferably be formed of material removed from the elongated member to form the enlarged cavity. A proximal end of the radioactive sourcewire is welded shut.

The above description and other features and advantages of the present invention will be appreciated and understood by those skilled in the art from the following detailed description, drawings and appended claims.

BRIEF DESCRIPTION OF THE DRAWINGS

Referring now to the drawings, wherein like elements are numbered alike in the several FIGURES.

DETAILED DESCRIPTION OF THE PREFERRED EMBODIMENT

Figure 1:
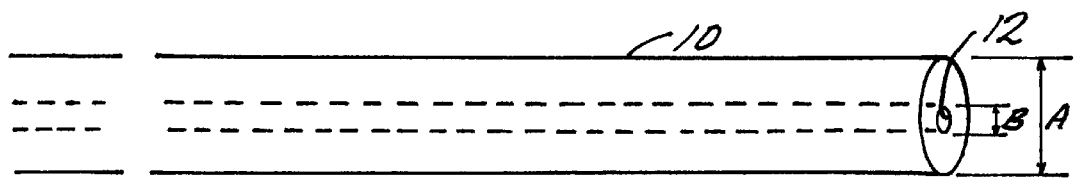
FIG. 1 is a perspective view of a thick walled tubular member.
Figure 2:
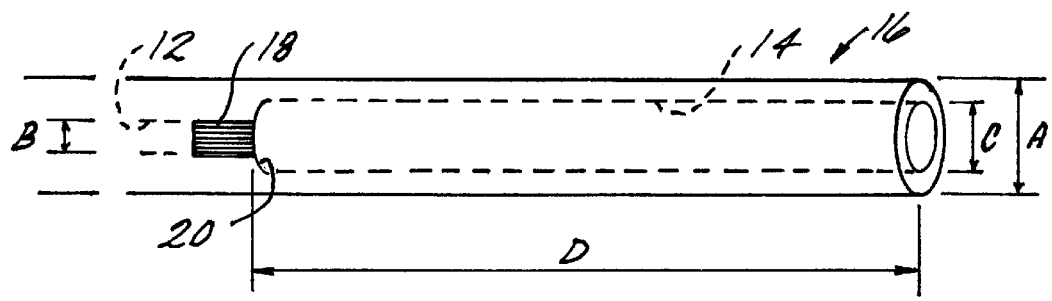
FIG. 2 is a perspective view, partially shown in section, of the thick wall tubular member of FIG. 1 with an enlarged cavity drilled in a distal end and a plug.
Figure 3:
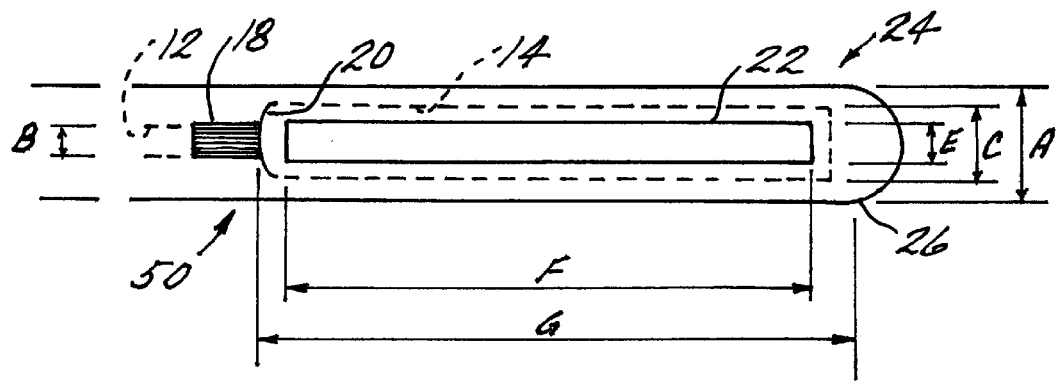
FIG. 3 is a side view of a novel sourcewire formed from the tubular member of FIG. 1 and enclosing a radioactive core.

Referring to FIGS. 1–3 there is disclosed a novel method of forming a radioactive sourcewire which has the strength of a solid sourcewire and flexibility of a tube-type sourcewire. The disclosed sourcewire is sufficiently small in diameter to reach the remote coronary arteries while incorporating a substantially long source cavity to contain a relatively long radioactive core.

Referring initially to FIG. 1, in order to form the disclosed sourcewire, an elongated generally thick walled tubular member 10 having an outer diameter A and an inner bore 12 having an inner diameter B is provided and modified to contain an elongated radioactive source or core.

By utilizing a generally thick walled tubular member 10 including relatively small diameter bore 12 therethrough as the initial stock material the resulting sourcewire will have the strength and flexibility of a solid wire while being able to have formed therein a cavity sufficiently long to retain an elongated radioactive core. An elongated source cavity is desirable, especially in relatively small diameter sourcewires, so that an elongated radioactive source may be incorporated into the sourcewire. By providing an elongated radioactive source, "stepping" or repeated positioning of the sourcewire, may be minimized or even eliminated to treat a given treatment zone. Further, the finished sourcewire will have greater pushability with less chance of kinking.

Preferably, tubular member 10 is formed of Nitinol or similar shape memory material such that after being bent or stressed the material will tend to re-assume its straight or prestressed shape when the stress is removed. Preferably, outer diameter A of tubular member 10 is approximately 0.0136 inches plus or minus 0.004 and inner diameter B of bore 12 is approximately 0.0045 inches plus or minus 0.0005 inches.

With specific reference to FIG. 2, an enlarged cavity 14 is drilled or counterbored within a distal end 16 of tubular member 10 by conventional drilling methods or laser or electron beam drilling methods. It should be noted that by using a thick walled tubular member 10 with full length bore 12 as the stock material, full length bore 12 acts as a pilot hole for drilling or enlarging cavity 14 in distal end 16 of tubular member 10 to ensure centering of cavity 14 within tubular member 10. The creation of an elongated source cavity is generally not possible where bores of approximately greater than approximately 20 mm length are attempted to be drilled by either conventional, or electron beam drilling through a solid wire as the drill often veers off the center line of the tubular member. Preferably, the resultant drilled cavity 14 has an overall diameter C of 0.0055 to 006 inches and an overall length D of approximately 32 mm.

A sourcewire may be formed from drilled tubular member 10 by inserting a radioactive source within cavity 14 and welding distal end 16 shut. Alternatively, the distal end 16 may be sealed by other methods. In one embodiment (not shown), the bore 12 and cavity 14 remain open to each other. Bore 12 may be sealed at one or more points along its length. Additionally, a proximal end of tubular member 10 may be welded or sealed shut.

In the preferred method, during the drilling of cavity 14, the resultant removed material from tubular member 10 is allowed to flow down to the junction between bore 12 and cavity 14 to form a plug 18. Preferably, the volume of material forming the plug is substantially equal to the volume of material removed, i.e., the difference in diameters of the initial bore 12 and the subsequent drilled cavity 14 over length D of the cavity 14. The plug material is caused to flow into bore 12 due to gravity or capillary action. Alternatively, suction applied from the proximal end or positive pressure applied to the plug material from the distal or drilling end may be used to induce the plug materially to flow partially or wholly into bore 12 to form plug 18. As shown, a proximal end of cavity 14 is preferably formed with a tapered region 20 which allows the resultant sourcewire to maintain a degree of flexibility at the junction between bore 12 and drilled cavity 14. The transitions between the thinner tube wall and the thicker tube wall will increase the flexibility of the segment containing the core and help to transfer the stress from the thinner wall to the thicker wall segment. This will greatly increase the cycle life of the sourcewire and help prevent breakage. The length of the tapered region 20 is preferably 2–3 mm (or greater).

Referring now to FIG. 3, in order to complete the disclosed sourcewire, a core 22 is inserted into drilled cavity 14. Core 22 preferably has an outer diameter E of 0.005 inches, or, depending on the size of the desired sourcewire, approximately 0.001 inches less than the diameter C of drilled cavity 14. Core 22 is preferably formed of a radioactive source or sources such as, for example, $Ir_{-192}$, $P_{-32}$, $C_{0-57}$, $C_{0-60}$, $C_{S-137}$, etc. Core 22 preferably has an overall length F of 30 mm which is approximately 2 mm less than the overall length D of drilled cavity 14.

Core 22 may be inserted into cavity 14 in an active radioactive state or may be inserted into cavity 14 in an inert state. When inserted into cavity 14 in an inert state, the entire sourcewire is subsequently irradiated to activate the radioactive core 22. Additionally, prior to irradiation, core 22 may be encapsulated in a neutron permeable material 24 which has a half life substantially less that of the core 22 such that upon irradiation of the encapsulated core 22, core 22 is irradiated and the encapsulation material is rendered inert within a short period of time. Preferably, the encapsulation material is titanium.

Preferably, in order to seal cavity 14, distal end 16 of the sourcewire assembly or tubular member 10 is welded shut. Upon welding shut distal end 16 of tubular member 10 the overall length G of drilled cavity 14 is reduced to approximately 31 mm. Subsequently, the welded distal end 24 may be machined or otherwise treated to form a generally rounded tip 26. This is necessary to ensure that the tip 26 of the completed sourcewire 50 does not snag or puncture through a catheter in which it is traveling.

In the embodiment having a seal or plug between the bore of the tubular member and the cavity, the core is thus completely sealed within the cavity in the event of breakage of the sourcewire below or proximal to the cavity segment. This safety feature will ensure that all radioactive material remain inside this segment and no radiation contamination will result in the event of breakage in the sourcewire.

The disclosed sourcewire generally includes an elongated thick walled hollow tubular member having a bore and an elongated enlarged cavity at a distal end thereof. The cavity contains a radioactive source and is sealed from the bore at a proximal end by a plug and at a distal end by a welded tip. Preferably, the plug is formed from the volume of material removed from a distal end of the tubular member to create the cavity. The welded tip is preferably rounded to facilitate movement through a catheter. The proximal most end of sourcewire 50 is preferably sealed.

The present sourcewire advantageously provides a simple sourcewire, which can be manufactured at small diameters, including a thick walled housing tube having a central bore, the housing tube providing strength to the construction comparable to solid wire systems, providing flexibility to the construction attributable to tube systems and providing excellent workability such that an elongated radioactive source cavity may be easily and consistently formed for sources up to and greater than approximately 20 millimeters in length.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A flexible sourcewire for radiation treatment of diseases within a body, comprising:
   a flexible, elongated housing tube having an outer surface, a bore defining a first interior wall surface along a proximal portion of the elongated housing tube, and a cavity defining a second interior wall surface along a distal portion of the elongated housing tube; and
   a radioactive source, disposed within the cavity, and wherein the elongated housing tube is sealed proximal to the radioactive source and at a distal end.

2. The flexible sourcewire in accordance with claim 1, wherein the radioactive source is one of $Ir_{-192}$, $P_{-32}$, $C_{0-57}$, $C_{0-60}$ or $C_{S-137}$.

3. The flexible sourcewire in accordance with claim 1, wherein the housing tube is sealed at a distal end by a tip welded to the distal end of the housing tube.

4. The flexible sourcewire in accordance with claim 3, wherein the tip is rounded at a distal end.

5. The flexible sourcewire in accordance with claim 1, wherein the housing tube is sealed at a proximal end.

6. The flexible sourcewire in accordance with claim 5, wherein a plug is welded to the proximal end of the housing tube.

7. The flexible sourcewire in accordance with claim 1, wherein the housing tube is sealed proximal to the cavity by excess material drilled from the cavity.

8. The flexible sourcewire in accordance with claim 7, wherein the volume of material sealing the housing tube proximal to the cavity is substantially equal to the volume of material drilled from the cavity.

9. The flexible sourcewire in accordance with claim 1, wherein the cavity includes a tapered region between the second inner surface of the cavity and the first inner surface of the bore.

10. The flexible sourcewire in accordance with claim 9, wherein the tapered region is abode about 1.5 millimeters in length.

11. The flexible sourcewire in accordance with claim 10, wherein the tapered region is between about 2 and about 4 millimeters in length.

12. The flexible sourcewire in accordance with claim 1, wherein the housing tube is contstructed from a nickel/titanium alloy.

13. The flexible sourcewire in accordance with claim 1, wherein the radioactive source is coated or encapsulated with a neutron permeable material prior to being inserted into the cavity.

14. The flexible sourcewire in accordance with claim 13, wherein the neutron permeable material has a half-life substantially less than that of the radioactive source.

15. The flexible sourcewire in accordance with claim 14, wherein the neutron permeable material is titanium.

16. The flexible sourcewire in accordance with claim 1, wherein the outer diameter of the elongated housing tube is less than about 0.015 inches.

17. The flexible sourcewire in accordance with claim 16, wherein the outer diameter of the elongated housing tube is less than about 0.014 inches.

18. The flexible sourcewire in accordance with claim 1, wherein the diameter of the bore is less than about half the outer diameter of the housing tube.

19. The flexible sourcewire in accordance with claim 18, wherein the diameter of the bore is less than about 0.006 inches.

20. The flexible sourcewire in accordance with claim 19, wherein the diameter of the bore is less than about 0.005 inches.

21. The flexible sourcewire in accordance with claim 19, wherein the diameter of the cavity is above about 0.006 and below about 0.007 inches.

22. The flexible sourcewire in accordance with claim 20, wherein the diameter of the cavity is above about 0.005 and below about 0.006 inches.

23. The flexible sourcewire in accordance with claim 1, wherein the cavity has a length greater than about 20 millimeters.

24. The flexible sourcewire in accordance with claim 23, wherein the cavity has a length between about 25 and about 35 millimeters.

25. The flexible soucewire in accordance with claim 24, wherein the cavity has a length between about 30 and 34 millimeters.

26. The flexible sourcewire in accordance with claim 1, wherein the radioactive source has an outer diameter of less than approximately 0.0015 inches than the diameter of the cavity.

27. The flexible sourcewire in accordance with claim 26, wherein the radioactive source has an outer diameter of approximately 0.001 inches less than the diameter of the cavity.

28. A process for manufacturing a radioactive sourcewire for irradiating diseased tissue, the process comprising:
   providing a flexible, elongated housing tube having an outer surface and a bore defining a first interior wall surface along a proximal portion of the elongated housing tube;
   drilling or counterboring a distal end of the elongated housing tube along the bore to a predetermined distance, thus forming a cavity defining a second interior wall surface along a distal portion of the elongated housing tube;
   inserting source material into the cavity; and
   sealing at least a portion of the housing tube.

29. The process of claim 28, further comprising drilling the elongated housing tube at a distal end along the bore such that drilled material flows into the bore.

30. The process of claim 29, wherein substantially all the drilled material flows into the bore, thereby providing a plug proximal to the cavity.

31. The process of claim 29, further comprising applying physical pressure to the displaced material such that the material is urged into the bore.

32. The process of claim 29, further comprising applying suction to the proximal end of the housing tube such that displaced material is urged into the bore.

33. The process of claim 28, wherein the drilling along the bore is controlled such that a tapered region is formed at a proximal end of the cavity, the tapered region defining an area between the second interior wall surface and the first interior wall surface.

34. The process of claim 33, wherein the wherein the tapered region is above about 1.5 millimeters in length.

35. The process of claim 34, wherein the tapered region is between about 2 and about 4 millimeters in length.

36. The process of claim 28, wherein the provided housing tube is a nickel/titanium alloy.

37. The process of claim 28, wherein the inserted radioactive source is coated or encapsulated with a neutron permeable material prior to being inserted into the cavity.

38. The process of claim 37, wherein the neutron permeable material has a half-life substantially less than that of the radioactive source.

39. The process of claim 38, wherein the neutron permeable material is titanium.

40. The process of claim 28, wherein the outer diameter of the provided elongated housing tube is less than about 0.015 inches.

41. The process of claim 40, wherein the outer diameter of the provided elongated housing tube is less than about 0.014 inches.

42. The process of claim 28, wherein the diameter of the bore is less than about half the outer diameter of the provided housing tube.

43. The process of claim 42, wherein the diameter of the bore is less than about 0.006 inches.

44. The process of claim 43, wherein the diameter of the bore is less than about 0.005 inches.

45. The process of claim 43, wherein the cavity is drilled to a diameter of above about 0.006 and below about 0.007 inches.

46. The process of claim 44, wherein the diameter of the cavity is above about 0.005 and below about 0.006 inches.

47. The process of claim 28, wherein the cavity is drilled to a length greater than about 20 millimeters.

48. The process of claim 47, wherein the cavity is drilled to a length between about 25 and about 35 millimeters.

49. The process of claim 48, wherein the cavity is drilled to a length between about 30 and 34 millimeters.

50. The process of claim 28, wherein the inserted radioactive source has an outer diameter of less than approximately 0.0015 inches than the diameter of the cavity.

51. The process of claim 50, wherein the inserted radioactive source has an outer diameter of approximately 0.001 inches less than the diameter of the cavity.

52. The process of claim 28, wherein the housing tube is sealed at a distal end.

53. The process of claim 52, wherein the housing tube is sealed at a distal end by a tip welded to the distal end of the housing tube.

54. The process of claim 53, wherein the tip is rounded at a distal end.

55. The process of claim 28, wherein the housing tube is sealed at a proximal end.

56. The process of claim 55, wherein a plug is welded to the proximal end of the housing tube.

\* \* \* \* \*